United States Patent [19]
McGrail

[11] Patent Number: 4,584,998
[45] Date of Patent: Apr. 29, 1986

[54] MULTI-PURPOSE TRACHEAL TUBE

[75] Inventor: Thomas W. McGrail, Glens Falls, N.Y.

[73] Assignee: Mallinckrodt, Inc., St. Louis, Mo.

[21] Appl. No.: 301,202

[22] Filed: Sep. 11, 1981

[51] Int. Cl.$^4$ ............................................. A61M 16/00
[52] U.S. Cl. ..................................... 128/604; 604/102
[58] Field of Search ........................ 128/344, 348–351, 128/246, 207.15; 609/96, 97, 98, 100, 102

[56] References Cited

U.S. PATENT DOCUMENTS

| | | |
|---|---|---|
| 2,493,326 | 1/1950 | Trinder . |
| 2,687,131 | 8/1954 | Raiche . |
| 3,725,522 | 4/1973 | Sheridan et al. . |
| 3,881,479 | 5/1975 | Carden . |
| 4,090,518 | 5/1978 | Elam . |
| 4,119,101 | 10/1978 | Igich . |
| 4,233,984 | 11/1980 | Walling . |
| 4,248,221 | 3/1981 | Winnard ........................ 128/207.15 |
| 4,270,530 | 6/1981 | Baum et al. . |
| 4,327,721 | 5/1982 | Goldin et al. ................. 128/207.15 |

FOREIGN PATENT DOCUMENTS 2380033 10/1978 France ............................ 128/349 B Primary Examiner—Stephen C. Pellegrino
Attorney, Agent, or Firm—Bernard, Rothwell & Brown

[57] ABSTRACT

A multi-purpose tracheal tube for use with high frequency ventilation. The tube is an endotracheal tube including up to three lumens, in addition to the primary lumen, which serve various functions to provide versatility in the treatment of patients. In cuffed tubes one of the lumens is used for inflating the cuff once the tube has been placed in the desired position in the trachea of the patient. Another lumen, referred to as the "insufflation lumen", is used to deliver oxygen or other gases by constant insufflation, intermittent jet ventilation or high frequency ventilation. The third lumen, when incorporated, is employed for monitoring and irrigation. The distal opening of the irrigation or monitoring lumen is located just inside the distal tip of the tube while the insufflation lumen opening is located rearwardly toward the proximal end of the tube relative to the irrigation or monitoring lumen opening.

7 Claims, 4 Drawing Figures

MULTI-PURPOSE TRACHEAL TUBE

BACKGROUND OF THE INVENTION

1. Field of the Invention

The invention relates to catheters used in the medical field and particularly endotracheal tubes.

2. Description of the Prior Art

Medico-surgical tubes may assume a variety of sizes, shapes and be provided with a variety of fluid openings, balloons or cuffs, couplings, or the like. Terminology applied to such devices by users, e.g. physicians, surgeons, hospitals, etc. frequently refer to them as catheters, e.g., rectal catheters, urethral catheters, hemostatic catheters and the like but in other cases they are referred to as tubes, e.g. endotracheal tubes, feeding tubes, suction tubes, drain tubes, and the like. For the sake of brevity in describing the improved devices of the invention and their method of production, the term "catheter" is employed throughout the specification and accompanying claims to encompass pertinent medico-surgical devices whether they be popularly referred to by the medical profession and other users as "catheters" or "tubes".

The modern trend in medical and surgical practices is toward the use of disposable catheters, i.e., those which may be used a single time on one patient and then discarded. Catheters of this type normally involve a plurality of lumens, one being the major lumen which serves to convey urine, blood serum, gases or any other fluid which may be introduced into or removed from the body of the patient and frequently a secondary lumen which is used as a conduit for air or liquid employed in inflating a balloon which forms a portion of the distal end of the catheter. Such a secondary lumen is attached to an inflation tube through which the air or liquid used to inflate the catheter balloon is introduced. These catheters, although providing a number of improvements over catheters which have existed before, suffer from some inadequacies particularly with the number or variety of functions that can be performed with a specific catheter.

Particularly when one is concerned with high frequency ventilation there is required the ability to provide oxygen or other gases at high rates and smaller tidal volumes, and it is often desirable to measure the pressure of the oxygen or other gas being emitted at the catheter distal end and to irrigate the vicinity for removal of fluids and other debris in the trachea. High frequency ventilation is a new technique in respiratory care which involves the ventilation of patients at higher rates and with smaller tidal volumes. This reduces peak and mean airway pressures encountered during mechanical ventilation and may facilitate the diffusion of gases across the alveolar capillary membrane. This technique has been called high frequency positive pressure ventilation (HFPPV), high frequency jet ventilation (HFJV) or high frequency oscillation (HFO) depending on the ventilatory rate employed and all of these techniques are generally known as high frequency ventilation (HFV).

With high frequency ventilation, particulary HFPPV and HFJV, as well as jet ventilation at conventional rates, the gases have been traditionally delivered through a transtracheal catheter inserted percutaneously or through a relatively small bore 10–14 (FR) insufflation catheter inserted orally or nasally until the distal tip is below the cords. In either case expired gases are allowed to passively escape past the indwelling cuffless catheter. Some studies have suggested that during high frequency ventilation the fresh gases should be introduced as close as possible to the carina for optimal gas exchange. This would indicate that the opening for any insufflation passage delivering these gases should be at the distal tip of the tube. However, there are disadvantages associated with this configuration. These include the alignment and direction problem associated with the location contiguous with the carina. For example, slight rotation of the tube can result in uneven ventilation of both lungs. Also, the exit of gases from the insufflation passage at high velocity may cause damage to the trachea mucosa. During the injection of gases entrainment can result in the generation of negative airway pressures in the region of the tube proximal to and immediately surrounding the insufflation lumen opening. Consequently, if there is a provision with the catheter to monitor airway pressure it should be measured sufficiently downstream or distal to the insufflation opening to minimize or eliminate the effect of entrainment and enhance the monitoring and irrigation function.

In the catheter described herein many of the problems discussed above have been eliminated or at least minimized by providing a multi-purpose device. The catheter is like a conventional tracheal tube except that it incorporates an insufflation passage or lumen within its wall. An additional lumen may be provided for irrigation or for monitoring airway pressure. In cuffed tubes the insufflation and irrigation/monitoring lumens are in addition to and generally larger than the secondary lumen provided for cuff inflation. The tube is configured such that the distal opening for the insufflation passage is displaced somewhat from the tip of the tube to avoid the distribution problem discussed above and to protect the patient from potential damage or trauma of high velocity gases. When the irrigation/monitoring lumen is included, its opening is located distal to the opening of the insufflation lumen and significantly spaced therefrom. If the pressure monitoring passage opening were located substantially closer to the opening for the insufflation lumen the pressure readout would be unusually low as a measure of entrainment present during the high velocity flow of the gas exiting from the insufflation lumen.

Another advantage of the multi-purpose catheter of the invention with the pathways for insufflation gases and for monitoring and irrigation is that there is always guaranteed a pathway for expired gases through the primary passage. Also, solutions delivered through the irrigation/monitoring passage or lumen can be effectively nebulized by the high velocity gas flow delivered through the insufflation passage or lumen. This configuration with the primary lumen also provides for scavenging of anesthestic gases, and positive end expiratory pressure (PEEP) can be maintained at any set level. This system also provides for additional aspiration protection through the use of a tracheal cuffed tube although for pediatric or neonatal applications the cuff is not necessary. By providing the additional lumen or lumens within the tube described above, it is a relatively simple matter to change to conventional therapy should that become necessary for whatever reason.

By having the passages or lumens extruded into the tube and otherwise configured as described above, a number of disadvantages are overcome. Certain problems have been associated with standard tracheal tubes where two cannulas have been passed through an external connector and into the main lumen of the tube. This latter approach compromises the cross-sectional area of the primary lumen. It becomes cumbersome and awkward to work with the number of tubes involved. And, the exact location of the distal tip of each cannula is difficult to ascertain. The patient must be disconnected from ventilatory support during suctioning or bronchoscopies. In this regard virtually all intubated patients need to be suctioned to remove accumulated secretions. While this procedure is being performed, the patient must be disconnected from ventilatory support or cumbersome external connectors must be employed. In critically ill patients, the oxygen evacuated from the lungs during suctioning, particularly at a time when no ventilatory support is possible, can result in serious hypoxia. If irrigation of the tracheal bronchial tree to aid the removal of secretions is necessary, the ventilator can be disconnected even longer. The multipurpose tracheal tube of the invention permits the delivery of air or oxygen by constant insufflation, jet ventilation, or HFV through the insufflation lumen during suctioning, thus preventing undesirable hypoxia. The irrigation can easily be accomplished using the irrigation/monitoring lumen.

SUMMARY OF THE INVENTION

The invention generally relates to a multi-purpose catheter usable in high frequency ventilation. More specifically it includes a catheter which is extruded of flexible plastic material and has a primary lumen of larger cross-sectional area when compared with other lumens in the tube. Up to three secondary lumens of smaller diameter are provided in the wall thickness of the tube and extend substantially the entire length of the tube. One of the secondary lumens is an insufflation lumen for delivering oxygen or other gases to a patient. An opening is cut into the interior wall of the catheter to communicate this secondary lumen with the primary lumen in the vicinity of the distal end of the catheter. Another secondary lumen may be employed for irrigation or for monitoring of airway pressure, and this lumen also includes an opening cut into the interior wall of the catheter in the vicinity of the distal end of the catheter. In cuffed tubes still another secondary lumen is employed; in this case an opening is cut through the exterior wall of the catheter in the vicinity of the distal end to communicate this lumen with an inflatable balloon fixed about the catheter and enveloping the opening.

DETAILED DESCRIPTION OF THE PREFERRED EMBODIMENT

Figure 1:
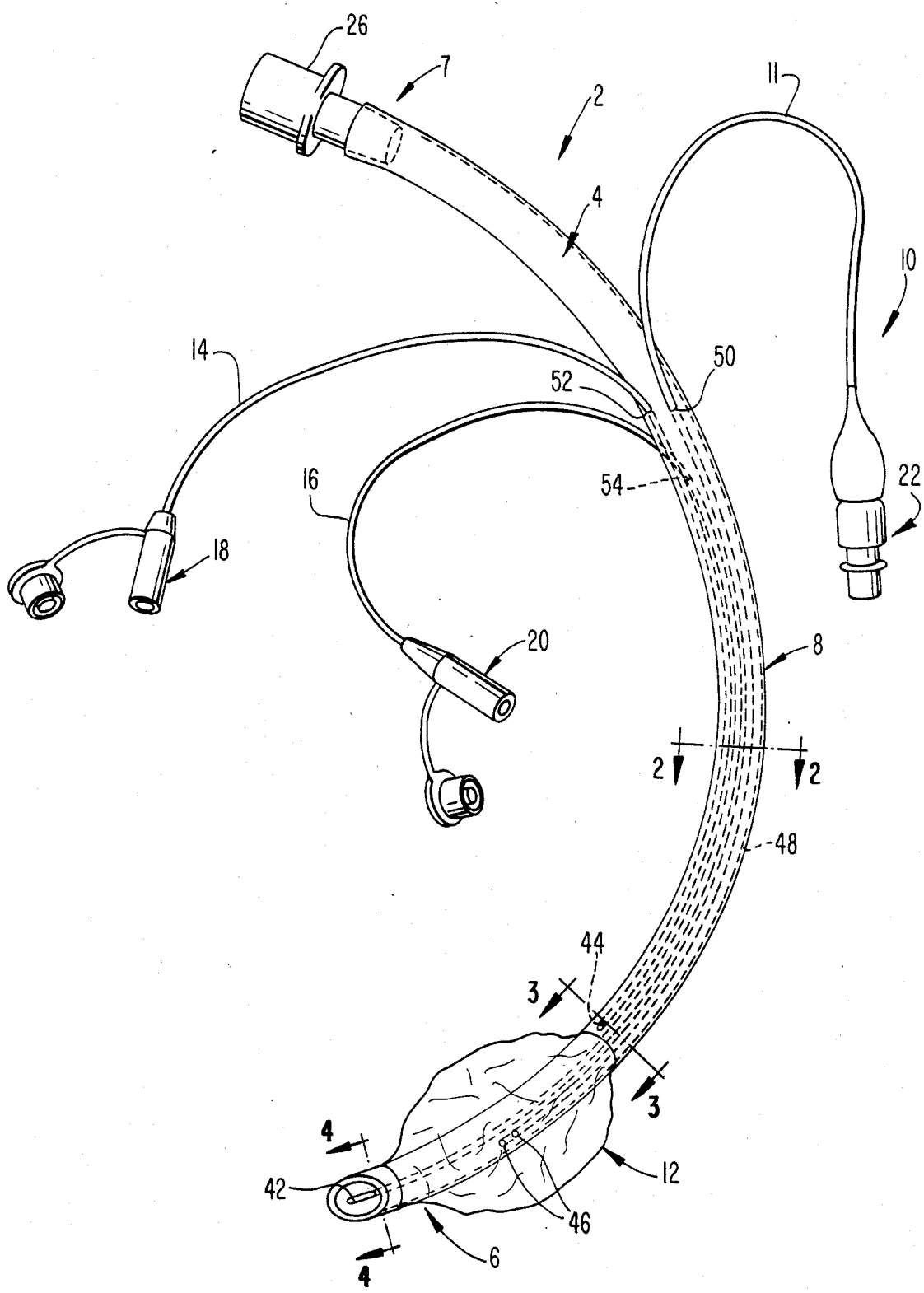
FIG. 1 is a perspective view of the multi-purpose tracheal tube of the invention.
Figure 2:
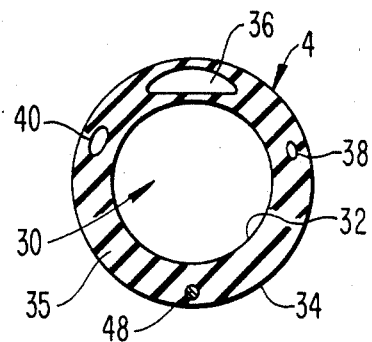
FIG. 2 is an enlarged cross-section of the tube taken along lines 2—2 of FIG. 1.

The endotracheal tube 2, in the form shown in FIG. 1, comprises a plastic tube 4, a distal end 6, a central body portion 8, a proximal end 7, inflation means 10 and inflatable balloon means 12. As will be understood by those skilled in the art, devices of this type will vary in size to accommodate different patients and operative conditions, e.g., a typical endotracheal tube would have an inside diameter of 8.0 mm., an outside diameter of 10.7 mm., a length of about 13 inches and will be of an arcuate form. The cross-section of the endotracheal tube as shown in FIG. 2 is representative of balloon-type catheters of the invention having a primary lumen generally in the center of the tube defined by the tube walls and three secondary lumens defined within the tube wall.

The tube 4, in the specific form shown in FIG. 1, defines a primary lumen 30 and the three secondary lumens 36, 38, and 40 all of which are of a smaller effective diameter than the wall thickness of tube 4 so that the lumens 36, 38, and 40 are formed completely within wall 35 of the tube 4. By this construction, inside wall 32 and outside wall 34 of tube 4 may be completely smooth and uninterrupted by protrusions, indentations, or the like. As a consequence the major lumen 30 can have its entire cross-section maintained throughout the entire length of the catheter 2 from the distal end 6 to the proximal end 7. Similarly, outside surface 34 of the catheter will present a smooth, uniform circular cross-section. The inside configuration of inside wall 32 may deviate somewhat from a circular configuration as can be seen in FIG. 2 to accommodate the size and number of lumens employed in a catheter. Specifically, in the configuration shown, inside wall 32 has a shape relative to the circular shape of outside wall 34 which provides a generally thicker wall in the vicinity of the secondary lumens when compared with the portion of the catheter where no lumens are provided. In this case all the lumens are in the upper half of the tube 4 when the tube is oriented as shown in FIG. 2; and, consequently, the thicker portion of the catheter is maintained in the upper portion of the tube as shown.

The catheter generally has the form of the endotracheal tube shown and described in U.S. Pat. No. 3,625,793. The tube 4 of the invention includes two additional lumens formed in the walls of the catheter tube during the extrusion process similar to the manner that a cuff inflation lumen 38 is formed in the wall as described in the aforementioned patent. These additional lumens include an insufflation lumen 36 which is the largest of the secondary lumens and an irrigation or monitoring lumen 40 which is of intermediate size, smaller than the insufflation lumen 36 but larger than the cuff inflation lumen 38. There is also provided in the tube an X-ray opaque line 48 which extends the entire length of the tube. The X-ray opaque line aids in locating the tube at the proper position in the trachea of the patient.

Using standard extrusion apparatus and techniques the tube 4 will present a smooth, highly polished or so-called "plate finish" surface on the inner and outer walls 32 and 34. However, the endotracheal tube 4 or any other catheter formed in accordance with the invention may be provided with a frosted surface in whole or in part, for the purposes and the methods described and claimed herein.

The inflation means 10 is formed of a section of extruded tubing 11 and a pilot balloon and valve 22 for the cuff inflation or any standard closure convenient for this purpose. The balloon and valve 22 are advantageously formed of flexible plastic material by injection molding but may be formed in any other suitable fashion from other materials such as semi-rigid plastics, rubber or the like by compression molding, dip coating or the like.

The balloon means 12 comprises an inflatable balloon cuff having a pair of opposed circular openings defined by short integral tubular extensions or shoulders. These shoulders have an inside diameter slightly smaller than the outside diameter of the tube 4. There are a number of ways of securing the balloon to the catheter, and an advantageous method is that described in U.S. Pat. No. 3,625,793 issued to Sheridan and Jackson on Dec. 7, 1971. The details of this will not be described herein but are included herein by reference to the aforementioned patent.

Communication between the cuff inflation lumen 38 and the cuff of balloon means 12 is accomplished by cutting an opening through the exterior wall of the tube adjacent the distal end thereof in communication with said secondary lumen. This is accomplished as shown in FIG. 1 by cutting notches 46 through the exterior wall sufficiently deep to communicate lumen 38 with the interior portion of the cuff when the cuff has been fixed in place over the notches 46. Another notch is formed near the proximal end of the tube at 50 for inserting inflation tube 11 into the cuff inflation lumen 38. There are a number of ways for inserting this inflation tube, a most advantageous of which is discussed at length in the aforementioned patent to Sheridan and Jackson.

The insufflation lumen 36 is formed in the same manner as cuff inflation lumen 38 during the extrusion process. However, as can be seen from the cross-section of the tube shown in FIG. 2, insufflation lumen 36 has a much larger cross-sectional area than cuff inflation lumen 38. The insufflation lumen 36 is preferably larger than the other secondary lumens, because its primary purpose is to deliver larger volumes in a brief time interval when used in high frequency ventilation. Since oxygen and other gases are delivered to the patient through this lumen, it is necessary that there be a relatively low resistance to flow to insure that the gas is delivered to the patient in the desired manner. It has been found for example in an 8 mm. tube the insufflation lumen has an equivalent diameter of about 2.5 mm. The effective or equivalent diameter of the insufflation lumen provides an area having a ratio to the area of the primary lumen preferably of about 1:7 to about 1:13. This ratio varies as the size of the tube varies.

The third lumen or irrigation/monitoring lumen 40 can be somewhat smaller than the insufflation lumen since bulk gas flow is typically not the same major consideration it is with the application of gases required through the insufflation lumen. However, since irrigation materials and pressure sensitive devices are used with the connection to the lumen 40 it is preferable that it be somewhat larger than the cuff inflation lumen to avoid undue pressure damping or clogging of the lumen. The size of this third lumen in an 8 mm. tube has an effective diameter of about 1.3 mm. In other words it is roughly about ¼ the cross-sectional area of the insufflation lumen. The size of the irrigation/monitoring lumen does not vary as much as that of the insufflation lumen for different tube sizes in order to insure that there is a reasonable response in measuring the pressure at the end of the lumen. Accordingly, lumen 40 maintains its effective diameter of about 0.6 mm. to 1.5 mm. or more depending on the size of the tube employed.

Connecting tubes 14 and 16 for the insufflation lumen and for the irrigation/monitoring lumen are secured in the same manner as inflation tube 11. That is, tube 4 is notched at 52 and 54 for inserting tubes 14 and 16 respectively into lumens 36 and 40. Each of these tubes 14 and 16 is provided with a connector 18 and 20 respectively at the end of a tube for connecting it to the appropriate source for ventilation or irrigation and monitoring. Proximal end 7 of tube 4 is similarly provided with a connector 26 to connect the primary lumen to the desired source or reservoir.

Figure 3:
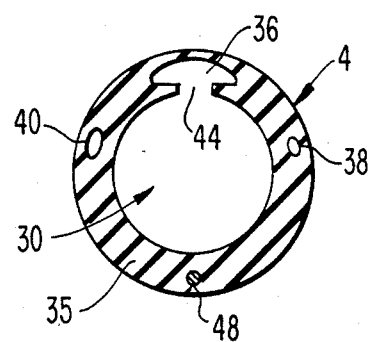
FIG. 3 is an enlarged cross-section of the tube taken along lines 3—3 of FIG. 1.
Figure 4:
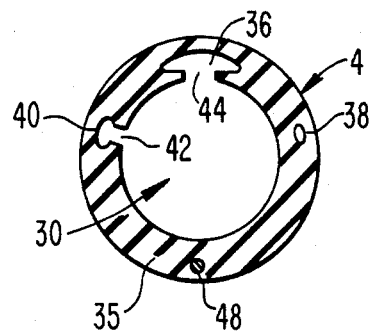
FIG. 4 is an enlarged cross-section of the tube taken along lines 4—4 of FIG. 1.

Unlike the cuff inflation lumen 38, insufflation lumen 36 and irrigation/monitoring lumen 40 ultimately communicate at the distal end of the tube with the inner wall 32. The exit openings of the irrigation/monitoring lumen 40 and the insufflation lumen 36 are spaced longitudinally from one another at the distal end of the tube 4. The distal opening 42 of the irrigation/monitoring lumen 40 is located just inside the distal tip of the tube. Insufflation lumen opening 44 is also inside the tube, but it is located about 5 cm. proximal to the irrigation/monitoring lumen opening 42. The relationship of these lumens can better be appreciated by viewing FIG. 1 in conjunction with FIGS. 3 and 4 which are cross sections taken at the insufflation and irrigation/monitoring lumen openings respectively. It has been determined that during high frequency ventilation, displacing the insufflation lumen from the tip results in a number of advantages in the operation of the tube 4. Rotation of the tube can be accomplished without causing unacceptable uneven ventilation which might otherwise result were the opening at the tip of the tube. Other advantages as discussed above include reduced potential of trauma to tracheal mucosa, accurate measuring of pressure and optimal nebulization of gases.

Although the insufflation lumen opening is located about 5 cm. proximal to the irrigation/monitoring lumen opening, it has been found that this optimal distance may vary from 2 to 10 cm. depending on the size of the tube and the rate of gas flow through the insufflation lumen. By locating the insufflation lumen opening 44 at this rearward position relative to the irrigation/monitoring lumen opening 42 more accurate pressure can be measured through the irrigation/monitoring lumen 40, and optimal nebulization of gases can be accomplished by this relative location of the openings. For example, one way of humidifying the gas delivered through the insufflation lumen is to connect the irrigation/monitoring lumen to a saline solution source. Saline solution delivered through lumen 40 is nebulized by the effect of gas delivered at high velocity through the insufflation lumen. Where the irrigation/monitoring lumen is not employed, the distal opening for the insufflation lumen may be disposed between 1 cm. and 10 cm. from the distal end of the catheter.

Another advantage of this type of system is the scavenging of anesthetic gases. Exhalation can be controlled and directed solely through the primary lumen 30. In this way the anesthetic gases can be piped out and directed to a particular collecting device rather than being dispersed into the operating room.

To form the distal openings for the insufflation and irrigation/monitoring lumens, a tool especially designed for this purpose is employed. This tool, referred to as a lumen stripper, is configured to be placed into the primary lumen 30, engage the inner wall 32 and strip that portion of the wall overlying a lumen to form the opening into the inner wall and a channel extending from the opening to a position adjacent the tip. When initially formed the lumens are closed by placing a bevelled end into a mold for producing a round, curved blunt like surface on the bevelled end of the tube as described at length in U.S. Pat. No. 3,625,793. Although other methods may be used to form these openings, the method described above in conjunction with the "lumen strippers" has proved most satisfactory.

The above has been a description of the preferred embodiment. It should be understood that this detailed description is not necessarily limiting and that the more full scope of applicant's invention is defined in the claims which follow.

I claim:
1. A balloon-type catheter comprising:
   (a) an extruded tube formed of flexible plastic material comprising a primary lumen and first, second, and third secondary lumens each of which has a smaller diameter than the primary lumen, all of said lumens extending substantially the entire length of the tube;
   (b) a proximal opening in said tube cut through the exterior tube wall into communication with the first secondary lumen, an inflation tube fixed through said proximal opening to said first secondary lumen in said tube;
   (c) a distal opening cut through the exterior wall of the catheter adjacent the distal end into communication with said first secondary lumen;
   (d) an inflatable balloon fixed about the catheter adjacent its distal end enveloping said distal opening of said first secondary lumen;
   (e) said second secondary lumen comprising an insufflation lumen having a proximal opening through the exterior wall of the tube, a second tube fixed through said proximal opening of said secondary lumen, a distal opening displaced proximally from the distal end of the tube cut through the interior wall of the catheter into communication with said second secondary lumen; and
   (f) said third secondary lumen comprising an irrigation or monitoring lumen having a proximal opening through the exterior walls of the tube, a third tube fixed through said proximal opening of said third secondary lumen, a distal opening adjacent the distal end, displaced from the distal opening of the second secondary lumen, forwardly toward the distal end of the catheter.

2. The catheter according to claim 1 wherein the distance between the distal openings of the second and third secondary lumens is between about two and ten centimeters.

3. The catheter according to claim 2 wherein the distance between the distal openings of the second and third secondary lumens is about five centimeters.

4. A catheter comprising:
   (a) an extruded tube formed of flexible plastic material comprising a primary lumen and a first secondary lumen, said first secondary lumen having a smaller diameter than the primary lumen and extending substantially the entire length of the tube:
   (b) said first secondary lumen being an insufflation lumen and having a proximal opening through the exterior wall of the tube, a first tube fixed through said proximal opening of said first secondary lumen, a first distal opening displaced proximally from the distal end of the tube cut through the interior wall of the catheter into communication with said first secondary lumen;
   (c) said distal opening being located between 1 cm and 10 cm from the distal end of the tube; and
   (d) a second secondary lumen for irrigation or monitoring airway pressure, said second secondary lumen having a second proximal opening through the exterior wall of the tube, a second tube fixed through said second proximal opening of said second secondary lumen, a second distal opening cut through the interior wall of the tube into communication with said second secondary lumen, said second distal opening being displaced forwardly toward the distal end of the catheter from said first distal opening.

5. The catheter according to claim 4 wherein the distance between said first and second distal openings is between about two and ten centimeters.

6. The catheter according to claim 4 wherein the distance between said first and second distal openings is about five centimeters.

7. A catheter comprising:
   (a) an extruded tube formed of flexible plastic material comprising a primary lumen and first and second secondary lumens each of which has a smaller diameter than the primary lumen, all of said lumens extending substantially the entire length of the tube;
   (b) said first secondary lumen comprising an insufflation lumen having a proximal opening through the exterior wall of the tube, a first tube fixed through said proximal opening of said first secondary lumen, a distal opening adjacent the distal end of the tube cut through the interior wall of the catheter into communication with said first secondary lumen; and
   (c) said second secondary lumen comprising an irrigation or monitoring lumen having a proximal opening through the exterior walls of the tube, a second tube fixed through said proximal opening of said second secondary lumen, a distal opening adjacent the distal end, displaced from the distal opening of the first secondary lumen, forwardly toward the distal end of the catheter.

* * * * *